(12) United States Patent
Bruins

(10) Patent No.: US 7,869,035 B2
(45) Date of Patent: Jan. 11, 2011

(54) SAMPLE TABLE FOR A FOOD ANALYZING DEVICE

(76) Inventor: Hans Joachim Bruins, Heerstrasse 7A, Munich (DE) 81247

( * ) Notice: Subject to any disclaimer, the term of this patent is extended or adjusted under 35 U.S.C. 154(b) by 0 days.

(21) Appl. No.: 12/297,976

(22) PCT Filed: Apr. 23, 2007

(86) PCT No.: PCT/EP2007/003552

§ 371 (c)(1), (2), (4) Date: Nov. 10, 2008

(87) PCT Pub. No.: WO2007/121974

PCT Pub. Date: Nov. 1, 2007

(65) Prior Publication Data

US 2009/0066950 A1   Mar. 12, 2009

(30) Foreign Application Priority Data

Apr. 24, 2006   (DE) .................. 10 2006 018 926

(51) Int. Cl.
*G01J 3/28* (2006.01)
(52) U.S. Cl. ...................................... 356/326
(58) Field of Classification Search ............... 356/326, 356/244, 432
See application file for complete search history.

(56) References Cited

U.S. PATENT DOCUMENTS

| 5,756,304 | A | 5/1998 | Jovanovich |
| 7,105,338 | B1 * | 9/2006 | Holmes et al. ........... 435/286.3 |
| 2006/0043300 | A1 * | 3/2006 | Campbell et al. ...... 250/339.09 |

FOREIGN PATENT DOCUMENTS

| DE | 3628155 A1 | 2/1988 |
| JP | 09275970 A | 10/1997 |
| WO | 03029845 A2 | 4/2003 |
| WO | 03089912 A1 | 10/2003 |
| WO | 2005093433 A1 | 10/2005 |

OTHER PUBLICATIONS

International Search Report for PCT/EP2007/003552.

* cited by examiner

*Primary Examiner*—Tarifur Chowdhury
*Assistant Examiner*—Abdullahi Nur
(74) *Attorney, Agent, or Firm*—Caesar, Rivise, Bernstein, Cohen & Pokotilow, Ltd.

(57) ABSTRACT

Disclosed is a sample table for a food analyzing device used for analyzing a food sample. Said sample table includes a sample holder (14) for receiving the food sample, a means for moving the sample holder (14), and a housing (12) that surrounds the moving means. The moving means and the sample holder (14) are magnetically coupled to each other such that the sample holder (14) can be moved relative to the housing (12) outside the housing (12). Also disclosed is a food analyzing device for spectroscopically analyzing food samples, said device encompassing such a sample table (10).

17 Claims, 5 Drawing Sheets

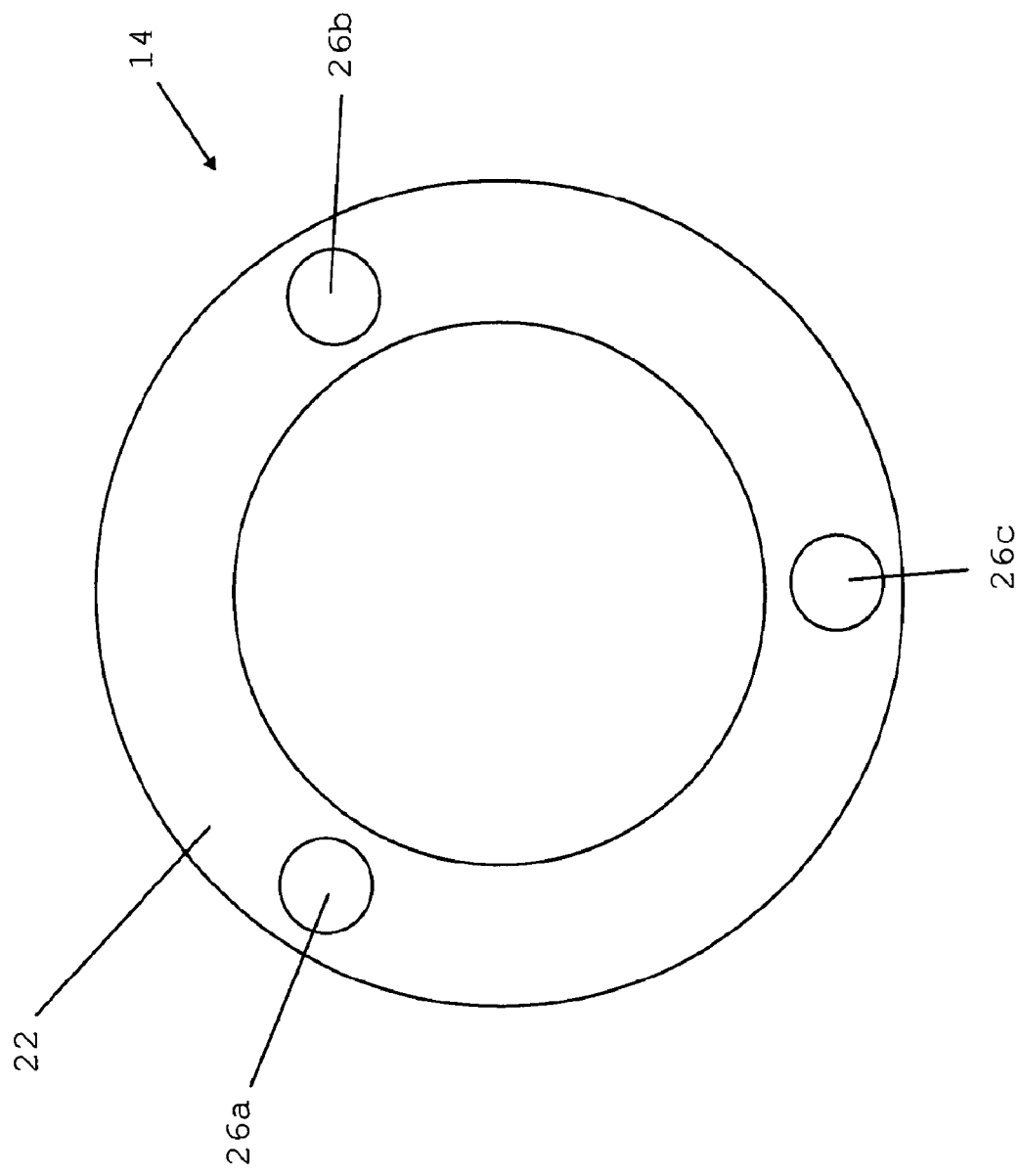

SAMPLE TABLE FOR A FOOD ANALYZING DEVICE

BACKGROUND OF THE INVENTION

The invention relates to a sample table for a food analyzing device.

Foods, such as cereals, bruised grain, pulses, flour, oil seeds, fish, and also meat and meat products for example, are regularly analyzed with regard to their composition. For this, spectrometers are used. These irradiate the food sample to be analyzed with a light beam of varying wavelength and measure the wavelength-dependent reflection or wavelength-dependent absorption of the light beam by the food sample.

Based on the reflection or absorption profile, it is possible to obtain information on the composition of the sample.

Since samples of foods are usually inhomogeneous in terms of their properties, it is necessary to carry out corresponding measurements at a large number of positions on a sample in order thus to obtain a mean value. To this end, the light beam is guided across the sample and a measurement of the absorption or reflection is carried out at a number of locations.

Such measurements are carried out regularly in the context of the incoming goods inspection and during the production process. Due to strict hygiene regulations, it is necessary to reliably prevent any contamination of the spectrometer.

Drives for the sample holder, by means of which the sample holder is moved in order to carry out measurements at different locations on the sample, have been found to be particularly problematic in this context. The drives usually have undercuts in which residues of food can accumulate and form germ hotspots.

In order to prevent these germ hotspots, in known spectrometers the light beam is guided across the sample. As a result, there is no need for a drive for the sample holder and germ hotspots are avoided. In order to guide the light beam, movable mirrors are used for example.

However, the control of these mirrors is complicated and susceptible to errors, particularly in harsh environmental conditions, such as in the incoming goods department for example.

The objective of the present invention is therefore to propose a sample table for a food analyzing device which alleviates the above disadvantages. In particular, the objective of the invention is to provide a simplified sample table and a food analyzing device which allow a rapid or simple spectroscopic analysis of a food sample and are easy to clean.

The invention achieves this objective by means of a sample table for a food analyzing device and a food analyzing device having the features of the invention.

SUMMARY OF THE INVENTION

One advantage of the sample table according to the invention is the fact that there is no need for guidance of the light beam. This reduces the number of parts to be actuated, as a result of which the sample table, or a food analyzing device which comprises a sample table according to the invention, is less susceptible to faults and is less expensive to produce.

Another advantage is the fact that the sample holder is easy to remove and to clean. It is thus possible for example to change and to clean the sample holder at regular intervals. No mechanical connections have to be released in order to remove the sample holder. Moreover, it is possible to configure the sample holder in such a way that it has no undercuts. As a result, accumulations of food and hence germ hotspots are avoided.

Another advantage of the present invention is the fact that a large number of sample holders can be held in stock, which can rapidly be connected to the rest of the sample table without having to release any mechanical connections.

Another advantage is the fact that the housing of the sample table can be designed such that it can be encapsulated in a watertight manner, so that the sample table can regularly be spray-cleaned. Such a type of cleaning is possible in a rapid and cost-effective manner and reliably prevents contamination of the sample table.

A sample holder is understood here to mean in particular a device into which a sample of food can be filled. However, a sample holder is also understood to mean in particular a device into which there can be inserted a further device, which in turn contains the sample of food. This latter device may be a Petri dish for example.

A movement means is understood to mean in particular a device which can move the sample holder on a circular path. The movement means is in particular designed to rotate the sample holder about an axis of rotation. If the sample holder is a sample holder for holding a Petri dish, the axis of rotation preferably runs through the base surface of the Petri dish, in particular through the center point thereof.

The housing is in particular designed in such a way that it has a top side which points upwards during operation of the sample table and which is substantially flat. The sample holder is then designed to slide on this flat surface. To this end, according to the invention, the sample holder couples magnetically to the movement means.

A magnetic coupling is understood here to mean that a movement of the movement means leads to a movement of the sample holder based on magnetic attraction or repulsion forces. It is particularly advantageous to design the housing such that it is free of undercuts, so that no germ hotspots can form.

In one preferred embodiment, the movement means comprises at least one drive magnet and the sample holder comprises at least one follower magnet.

These are preferably coupled in such a way that a different polarity (north or south pole) of the follower magnet and drive magnet are arranged opposite one another on both sides of the housing. For example, if a north pole side of the drive magnet bears against the housing, then a south pole side of the follower magnet bears against the opposite side. The magnetic field lines then pass through the housing in such a way that, when the drive magnet is moved by the movement means, the follower magnet is subjected to a magnetic force, as a result of which it follows the moving drive magnet.

Preferably, the movement means is designed to move the sample holder on a circular path and/or to rotate it about its horizontal axis. As an alternative or also in addition, an x-y table is provided in order to be able to position the sample holder freely in space. The x-y plane here runs parallel to the housing part on which the sample holder rests during operation. This is preferably a horizontal top side of the housing.

Preferably, the sample table has a window for the passage of light, wherein the window is arranged in such a way that a light beam emerging vertically from the window impinges on the sample of food held in the sample holder. Depending on the wavelength spectrum intended for the measurement, the window is substantially transparent for the appropriate wavelengths.

Preferably, the sample holder is designed to hold a Petri dish. In particular, the sample holder is designed to hold Petri dishes having a diameter of more than 30 mm, in particular of more than 50 mm, in particular of more than 70 mm, in particular of more than 90 mm. In particular, the sample holder is designed to hold Petri dishes having a diameter of less than 300 mm, in particular of less than 200 mm, in particular of less than 150 mm, in particular of less than 120 mm.

The housing is preferably designed to be watertight. This means that it can be sprayed in particular with a water jet at a line pressure of 4 MPa, without water penetrating into the housing. The housing is moreover considered to be watertight when it can be placed under water in such a way that it is completely covered by water, and nevertheless no water penetrates into the housing.

The housing is preferably made from V2A or V4A steel. As an alternative, the housing is made from aluminum or lacquered plastic. The housing is preferably non-magnetic. In the context of the invention, preference is given to housing materials which can be disinfected, in particular disinfectable steel. The surface of the steel is designed in such a way that it is easy to disinfect.

Advantageously, the sample table can be switched on and off from outside, for which purpose, for example, a switch is arranged inside the housing which can be controlled from outside without any mechanical change to the surface of the housing. Such a switch may be a Reed contact influenced by a magnet held outside. However, it is also possible to use other switches, for example those which react to the housing being touched at a certain location.

The sample table can preferably be remotely controlled and read in a wireless manner. This offers the advantage that a data transmission from and to the sample table is possible without adversely affecting its suitability for disinfection. The sample table preferably comprises a display screen, particularly preferably a touchscreen, wherein the display screen is suitable for the passage of electromagnetic radiation, and comprises a transmitter arranged inside the housing for transmitting electromagnetic signals, wherein the transmitter is arranged relative to the display screen, in particular the touchscreen, in such a way that a transmission of electromagnetic signals from and to the transmitter through the display screen is possible. As an alternative, other possibilities can also be used for allowing a wireless transmission of signals, for example an infrared interface. The display screen may also be replaced by another suitable electromagnetic opening in the housing, for example by a glass window. However, the display screen offers the advantage that its surface can be designed such that it can be disinfected, so that simple operation of the sample table is possible without restricting the ability of the housing to be disinfected. As the transmitter, use may be made for example of Bluetooth, WLAN or other suitable interfaces.

Preferably, the dissipation of heat generated in the housing during operation takes place through the housing. To this end, heat dissipating means may be arranged in the housing and may be connected to the housing, for example aluminum bridges or heat transfer paste, so that the housing acts as a cooling body. The heat dissipating means are arranged between components which generate heat, for example a transformer, and the housing. The heat dissipating means may also be a fixing frame, which carries a motor or the like and is fixed to the housing. This makes cooling slots unnecessary.

BRIEF DESCRIPTION OF SEVERAL VIEWS OF THE DRAWINGS

The invention will be explained in more detail below with reference to the appended drawings, in which:

FIG. 5 shows a schematic view of a sample holder according to the invention for a food analyzing device.

DETAILED DESCRIPTION OF PREFERRED EMBODIMENTS

Figure 1:
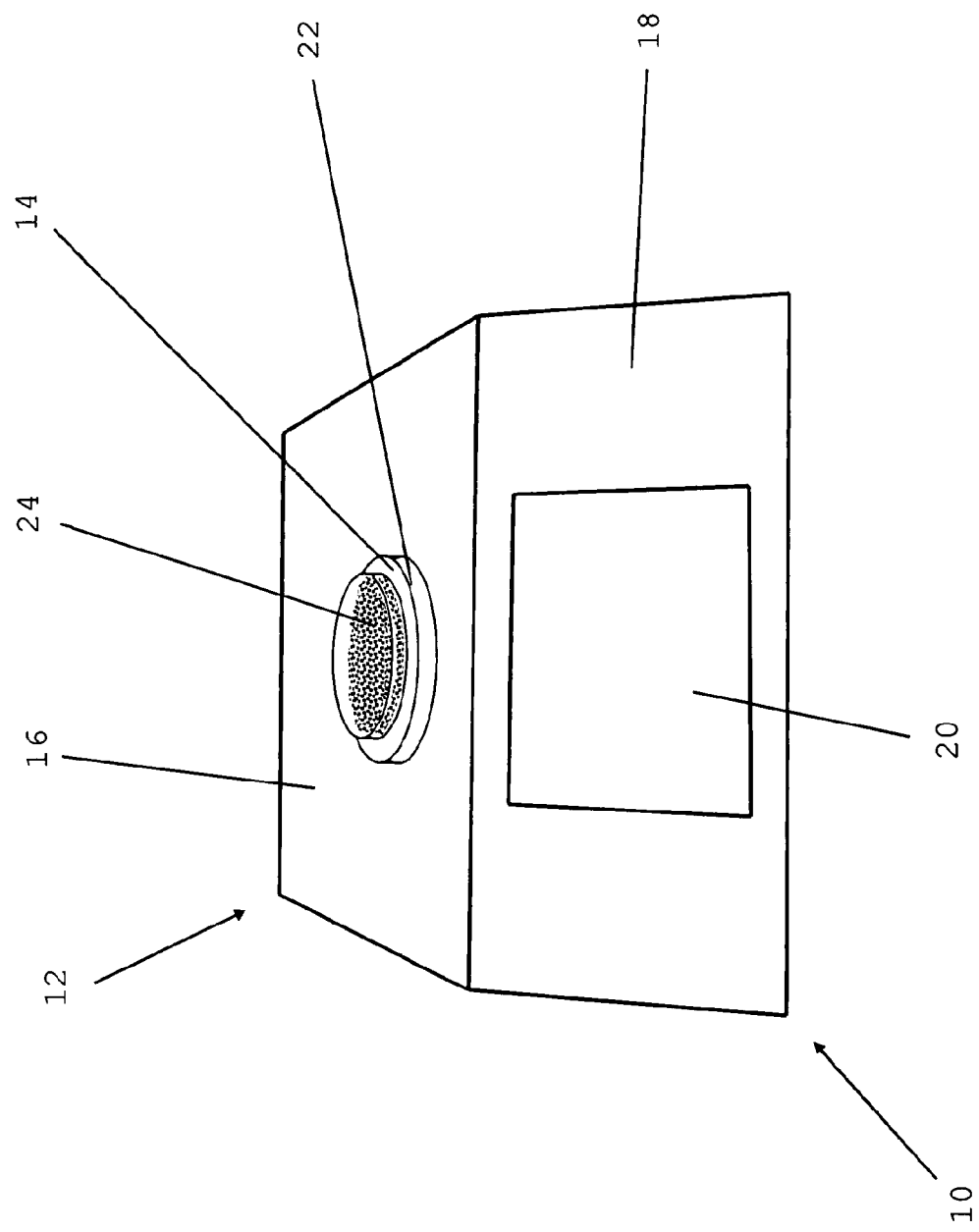
FIG. 1 shows a perspective view of a food analyzing device according to the invention with a sample table according to the invention, in the sample holder of which a sample of food is held.

FIG. 1 shows a sample table 10 which includes a housing 12 and a sample holder 14. The housing 12 has a top side 16, which runs substantially horizontally, and a front side 18, which is inclined at an angle of approximately 45° with respect to the horizontal. The housing 12 consists of V2A steel. In an alternative embodiment, the housing is made from V4A steel. The surface of the housing 12 is treated in such a way that it can be disinfected, so that the housing 12 is suitable for food analysis. Incorporated in the front side 18 is a display 20 for displaying measurement results and for displaying operating menus. The display 20 is preferably permeable to electromagnetic radiation. A touchscreen offers the advantage that it is possible to control the menus via the touchscreen. The housing 12 is preferably closed on all sides and is free of ventilation slots.

The sample holder 14 comprises a plastic ring 22, the internal diameter of which is such that a Petri dish 24 having a diameter of 100 mm can be held. The sample holder 14 is designed to slide on the top side 16 of the housing 12 with low-friction.

Incorporated in the plastic ring 22 of the sample holder 14 are three follower magnets 26*a*, 26*b*, 26*c* (FIG. 5) (not shown in FIG. 1). The magnets 26*a*, 26*b*, 26*c* end flush with the underside of the plastic ring 22 facing towards the top side 16 of the housing 12. The north poles of the follower magnets 26*a*, 26*b*, 26*c* point upward during operation of the sample table 10.

Figure 2:
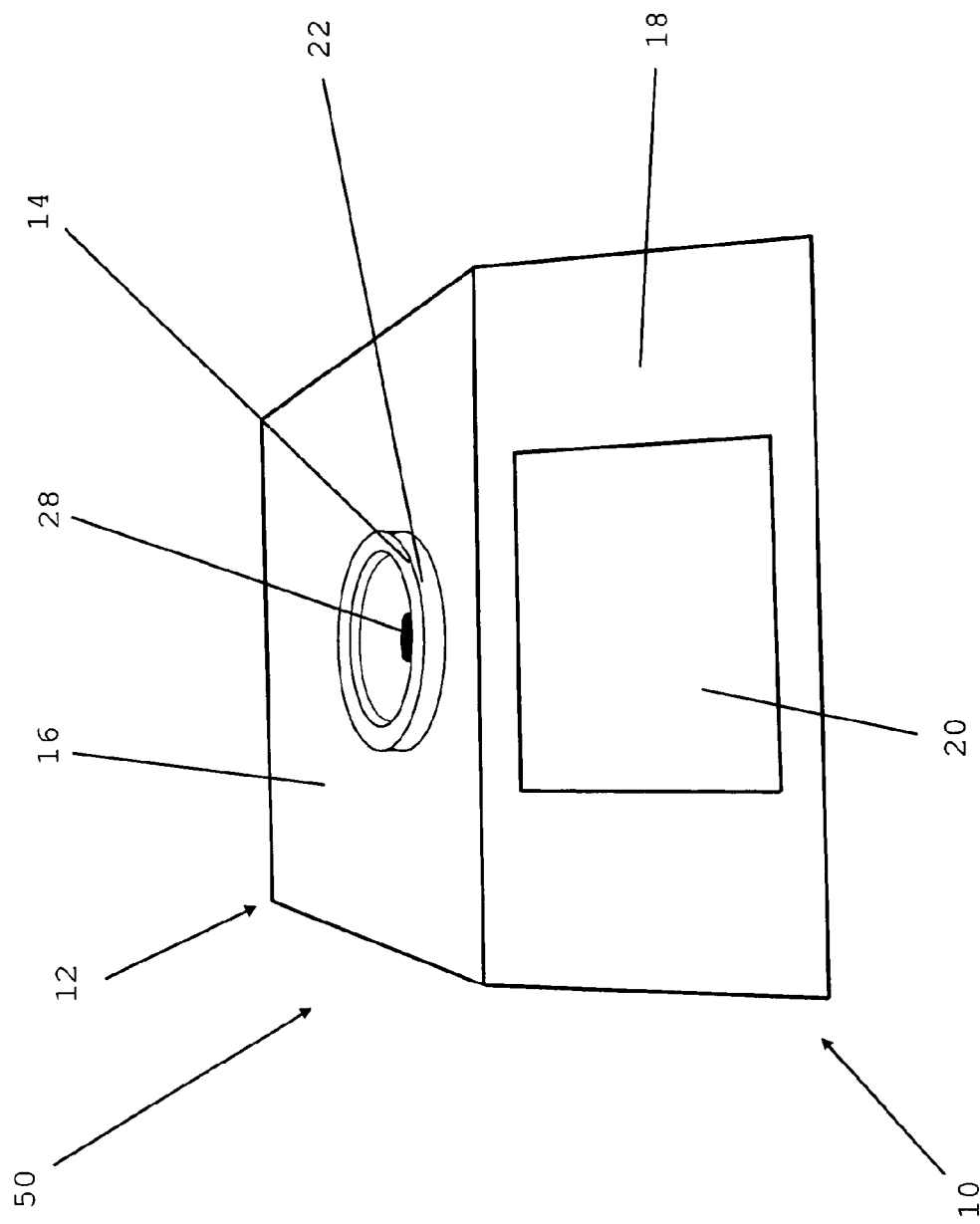
FIG. 2 shows a food analyzing device according to FIG. 1, but without a sample of food.

FIG. 2 shows the sample table 10 with the sample holder 14, but the latter is not holding a Petri dish. A window 28 is formed in the top side 16 of the housing 12. This window is an opening in the top side 16 of the housing 12, which is covered by a transparent pane. The window is designed to allow to pass, substantially free of absorption, light in the spectral range from 380 to 2500 nm, preferably in the spectral range from 730 nm to 1100 nm.

Figure 4:
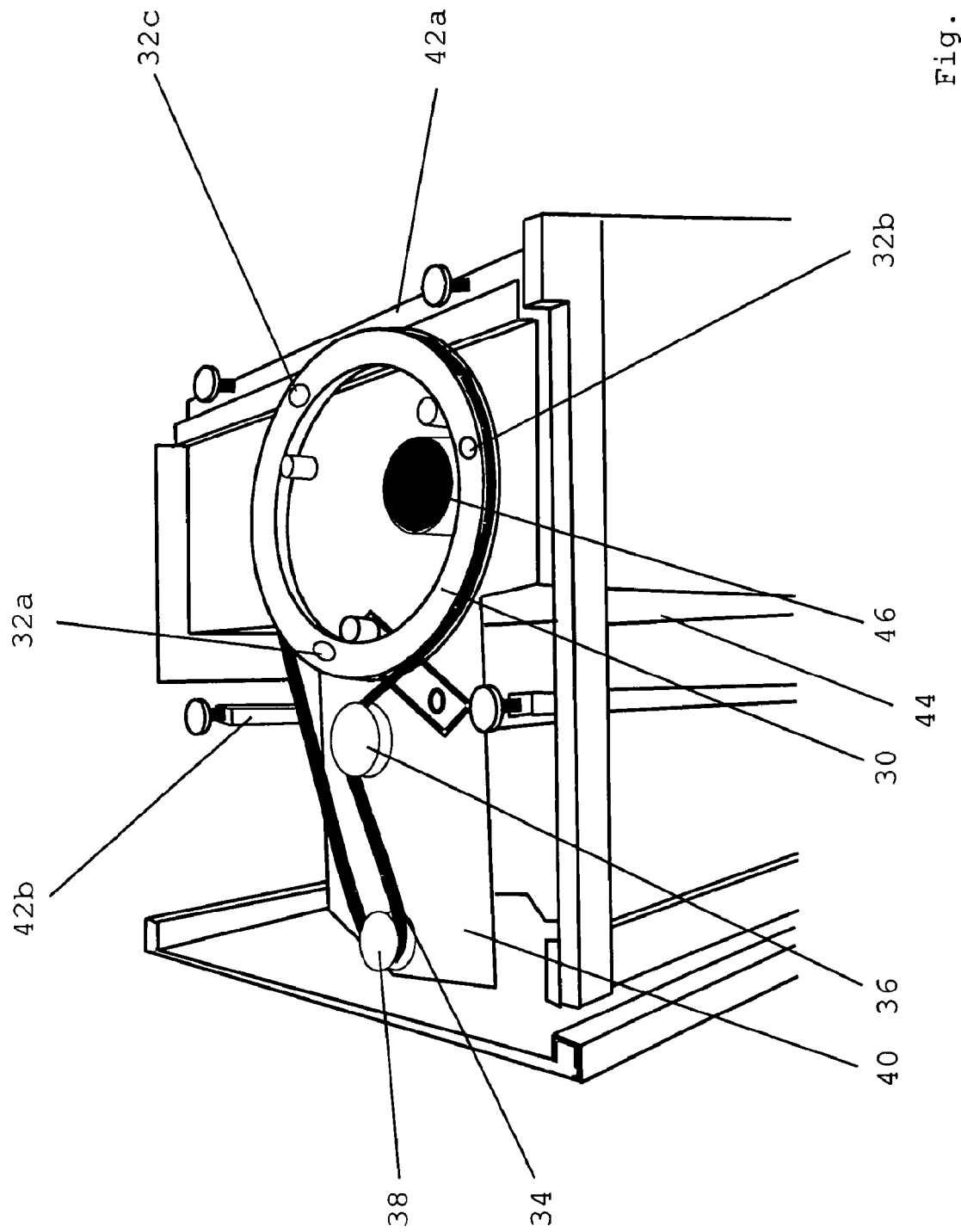
FIG. 4 shows an internal view of a food analyzing device according to the invention.

FIG. 4 shows the sample table 10, wherein the top side 16 and the front side 18 have been removed from the housing 12. Located directly below the top side 16 (not present here) of the housing 12 is a drive ring 30 which has the same diameter as the plastic ring 22 (cf. FIG. 1).

Incorporated in the drive ring 30 are three drive magnets 32*a*, 32*b*, 32*c* which end flush with the top side of the drive ring 30. The north poles of the drive magnets 32*a*, 32*b*, 32*c* point upward and, during operation, interact with the downward-pointing south poles of the follower magnets 26a, 26b, 26c. The drive ring 30 is arranged directly below the top side 16 of the housing 12.

The drive ring 30 is driven via a belt 34 in the form of a toothed belt, which in turn is driven by an electric motor 36. The movement of the belt 34 is recorded here by an angle sensor 38, which is connected to a central control system (not shown here), and controls the rotation of the drive ring.

The drive ring 30 and the electric motor 36 are arranged on a carriage 40 which can be displaced in translation via two guide rails 42a, 42b.

During operation of the sample table 10, the electric motor 36, via the belt 34, rotates the drive ring 30 so that the drive magnets 32a, 32b, 32c directly below the top side 16 of the housing 12 rotate. As a result, the follower magnets 26a, 26b, 26c, which are arranged on the opposite side of the top side 16 of the housing 12, are subjected to a magnetic force so that the sample holder 14 follows the movement of the drive ring 30.

In the present embodiment, both the drive magnets 32a, 32b, 32c and the follower magnets 26a, 26b, 26c are distributed at equal spacings around the circumference of the drive ring 30 and the plastic ring 22 respectively. Alternatively, it is also possible for 2, 4, 5, 6, 7, 8, 9, 10 or more than 10 drive magnets and follower magnets to be provided.

The drive magnets and follower magnets are selected here to be so strong that a reliable movement of the plastic ring 22 is ensured when the distance between the drive magnets 32a, 32b, 32c and the follower magnets 26a, 26b, 26c is 4 mm. The follower magnets and drive magnets are permanent rare earth magnets. Magnets made from cobalt/samarium or neodymium/iron/boron compounds or alloys have proven to be suitable. However, it is not absolutely necessary to provide both drive magnets and follower magnets. If the drive magnets or follower magnets are designed to be strong enough, it is possible to omit follower magnets or drive magnets respectively. Instead, blocks of ferromagnetic material are then provided.

FIG. 4 shows, in addition to the sample table 10, a light source 44 for generating light of different wavelengths. The light source 44 comprises for example a white light source and a monochromator, as known from conventional spectrophotometers. The light leaves the light source 44 through an outlet opening 46. This outlet opening 46 is arranged in such a way that a light beam emerging from the outlet opening 46 passes through the window 28 in the top side 16 of the housing 12.

The outlet opening 46 is arranged here relative to the drive ring 30 in such a way that the outlet opening 46 is never covered by the drive ring 30, even during rotation of the drive ring 30. Accordingly, the sample holder 14 is designed in such a way that a light beam emerging from the window 28 is not occluded by the plastic ring 22. Even during the rotation of the drive ring 30 and plastic ring 22, therefore, light can always pass through the outlet opening 46 and the window 28 and impinge on the Petri dish 24.

By virtue of the carriage 40, the drive ring 30 can be displaced so that light can emerge through the outlet opening 46 without impinging on a sample held in the sample holder 14. In this way, reference measurements and calibration measurements can be carried out.

If light impinges as described on a food located in the Petri dish 24, said food reflects the light at a rate dependent on the wavelength. Some of the light thus reflected passes through the window 28 back into the housing 12 and through the outlet opening 46 into an analyzing device 48 (not shown here).

The analyzing device 48 detects the radiation reflected by the sample of food and forwards it to a control system (likewise not shown). The control system comprises an evaluation unit for evaluating the measurement data.

Figure 3:
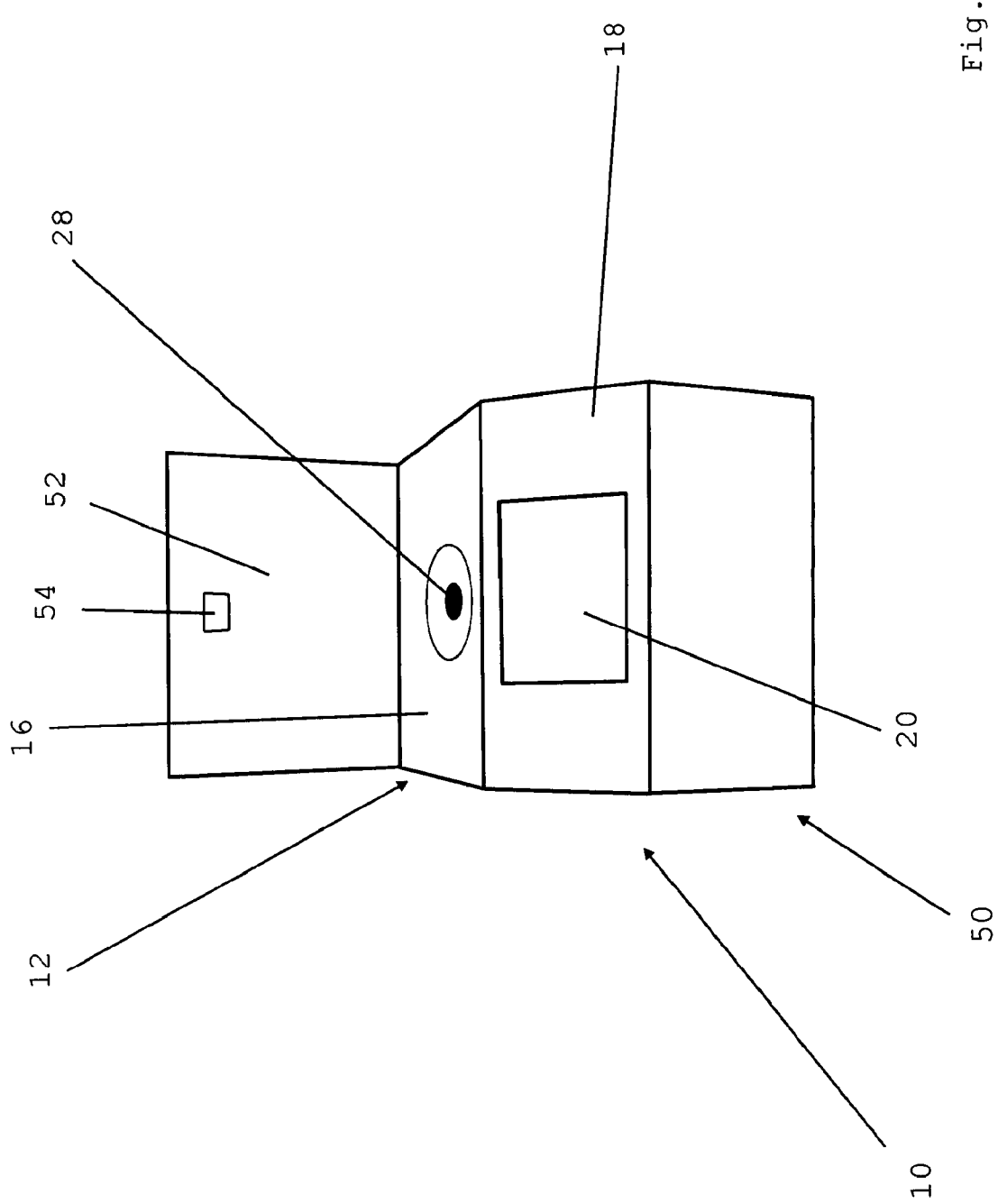
FIG. 3 shows the food analyzing device according to FIG. 1, which additionally has a cover.

FIG. 3 shows an alternative embodiment of a food analyzing device 50, which includes a sample table 10 and a light source 44 as described above. In addition, the food analyzing device 50 comprises a cover 52 in which a detector 54 is incorporated. This detector 54 detects light which has passed through the sample of food, as a function of the wavelength of the light.

The measurement signals received by the detector 54 are forwarded via electronic contacts (not shown here) or via a radio interface to the central control system (likewise not shown here) of the food analyzing device 50. As an alternative to the detector 54, the cover 52 comprises a double mirror 56 or a prism for deflecting the light beam back into the housing 12. In this case, a detector for detecting the quantity of light that has passed through the sample of food is provided in the housing 12.

It is possible to configure the food analyzing device 50 in such a way that both the light reflected by the sample of food and also the transmitted light can be measured.

A method according to the invention is carried out in that a sample of food is brought into the beam path of a food analyzing device, an absorption and/or transmission measurement is carried out, and then the sample is moved by a predefined amount. This movement is preferably carried out by means of a device according to the invention.

The invention claimed is:

1. A sample table for a food analyzing device for analyzing a sample of food, comprising
    a housing having a top side,
    a sample holder for holding the sample of food, said sample holder being adapted to rotatably slide on the top side of the housing and comprising at least one follower magnet or at least one ferromagnetic sample holder block, and
    a movement means for moving the sample holder, said movement means comprising an electric motor and a drive ring, said drive ring being rotatably arranged below the top side of the housing, carrying at least one drive magnet or at least one ferromagnetic material block and being coupled to the electric motor,
    wherein the housing surrounds (a) the electric motor, (b) the drive ring and (c) the at least one drive magnet or the at least one ferromagnetic drive ring block, and wherein the movement means and the sample holder are magnetically coupled so that the sample holder outside the housing can be rotated by a magnetic force between the sample holder and the drive ring.

2. The sample table according to claim 1, wherein the movement means further comprises at least one drive magnet, and the sample holder comprises the at least one follower magnet for interacting with the at least one drive magnet, so that the sample holder can be moved relative to the housing as a result of the interaction of the magnets.

3. The sample table according to claim 1, wherein the movement means further comprises a displacement unit for displacing the sample holder in translation relative to the housing.

4. The sample table according to claim 1, wherein the drive ring comprises three high-power magnets.

5. The sample table according to claim 1, wherein a window for the passage of light is arranged in the housing in such a way that a light beam emerging from the window impinges on the sample of food held in the sample holder.

6. The sample table according to claim 5, wherein the window is arranged in the housing in such a way that a light beam vertically emerging from the window impinges on the sample of food held in the sample holder.

7. The sample table according to claim 1, wherein the sample holder is designed to hold a Petri dish.

8. The sample table according to claim 1, wherein the housing is watertight.

9. The sample table according to claim 1, wherein the housing is made from non-magnetic material.

10. The sample table according to claim 1, further comprising a display screen, which is suitable for the passage of electromagnetic radiation, and a transmitter arranged inside the housing for transmitting electromagnetic signals, wherein the transmitter is arranged relative to the display screen in such a way that a transmission of electromagnetic signals from and to the transmitter through the display screen is possible.

11. The sample table according to claim 10, wherein the display screen comprises a touchscreen.

12. A food analyzing device for a spectroscopic analysis of samples of food, comprising:
   a sample table according to claim 1, which further comprises:
      a light source enclosed by the housing and
      a window for the passage of light from the light source, wherein the sample holder is arranged with respect to the window in such a way that, during operation of the food analyzing device, light from the light source impinges on the sample of food held in the sample holder, and
   means for analyzing a physical parameter which is characteristic of an interaction of the sample with light from the light source.

13. The food analyzing device according to claim 12, wherein the means for analyzing a physical parameter is adapted to analyze a wavelength-dependent absorption, and is arranged in the housing.

14. The food analyzing device according to claim 12, further comprising a mirror for reflecting light from the light source, which has passed through the sample, back into the housing.

15. A food analyzing device for a spectroscopic analysis of samples of food, comprising:
   a sample table according to claim 1, which further comprises:
      a light source enclosed by the housing and
      a window for the passage of light from the light source, wherein the sample holder is arranged with respect to the window in such a way that, during operation of the food analyzing device, light from the light source impinges on the sample of food held in the sample holder, and
   a spectrometer adapted to analyze a wavelength-dependent absorption of the light from the light source by the sample of food.

16. A sample table for a food analyzing device for analyzing a sample of food, comprising
   a housing having a top side,
   a sample holder for holding the sample of food, said sample holder being adapted to rotatably slide on the top side of the housing and comprising at least one follower magnet or at least one ferromagnetic sample holder block,
   an electric motor, and
   a drive ring coupled to the electric motor, rotatably arranged below the top side of the housing, and carrying at least one drive magnet or at least one ferromagnetic material block,
   wherein the housing surrounds (a) the electric motor, (b) the drive ring and (c) the at least one drive magnet or the at least one ferromagnetic drive ring block, and wherein the drive ring and the sample holder are magnetically coupled so that the sample holder outside the housing can be rotated by a magnetic force between the sample holder and the drive ring.

17. A food analyzing device for a spectroscopic analysis of samples of food, comprising:
   a sample table according to claim 16, which further comprises a light source enclosed by the housing and a window for the passage of light from the light source, wherein the sample holder is arranged with respect to the window in such a way that, during operation of the food analyzing device, light from the light source impinges on the sample of food held in the sample holder, and
   a spectrometer adapted to analyze a wavelength-dependent absorption of the light from the light source by the sample of food.

* * * * *